United States Patent [19]

Moore et al.

[11] Patent Number: 5,443,830
[45] Date of Patent: Aug. 22, 1995

[54] DRINK CONTAINING MUCILAGINOUS POLYSACCHARIDES AND ITS PREPARATION

[75] Inventors: D. Eric Moore, Richardson; Bill H. McAnalley, Grand Prairie, both of Tex.

[73] Assignee: Carrington Laboratories, Inc., Irving, Tex.

[21] Appl. No.: 136,076

[22] Filed: Oct. 13, 1993

Related U.S. Application Data

[60] Continuation-in-part of Ser. No. 864,583, Apr. 7, 1992, Pat. No. 5,308,838, which is a division of Ser. No. 558,905, Jul. 27, 1990, Pat. No. 5,118,673, which is a continuation-in-part of Ser. No. 229,164, Aug. 5, 1988, Pat. No. 5,106,616, which is a continuation-in-part of Ser. No. 144,872, Jan. 14, 1988, Pat. No. 4,851,224, which is a continuation-in-part of Ser. No. 869,261, Jun. 5, 1986, Pat. No. 4,735,935, which is a continuation-in-part of Ser. No. 810,025, Dec. 17, 1985, abandoned, which is a continuation-in-part of Ser. No. 754,859, Jul. 12, 1985, abandoned, which is a continuation-in-part of Ser. No. 750,321, Jun. 28, 1985, abandoned, which is a continuation-in-part of Ser. No. 649,967, Sep. 12, 1984, abandoned, which is a continuation of Ser. No. 375,720, May 7, 1982, abandoned.

[51] Int. Cl.[6] .................. A61K 35/78; A61K 31/715; C08B 37/00

[52] U.S. Cl. .................... 424/195.1; 426/72; 426/74; 426/590; 426/615; 514/25; 514/54; 514/458; 536/123; 536/124

[58] Field of Search ................. 424/195.1; 514/25, 54, 514/458; 536/123, 124; 426/72, 590, 615, 74

[56] References Cited

U.S. PATENT DOCUMENTS

| | | | |
|---|---|---|---|
| 4,917,890 | 4/1990 | McAnalley | 424/195.1 |
| 4,959,214 | 9/1990 | McAnalley | 424/195.1 |
| 4,966,892 | 10/1990 | McAnalley | 515/54 |

OTHER PUBLICATIONS

Chem. Abst. 96: 18880d, 1982.

*Primary Examiner*—Douglas W. Robinson
*Assistant Examiner*—Howard C. Lee
*Attorney, Agent, or Firm*—Hitt Chwang & Gaines

[57] ABSTRACT

A drink and a concentrate containing alcohol-precipitated mucilaginous polysaccharides from aloe vera leaves and its preparation is disclosed. Aloe vera mucilaginous polysaccharides, including acemannan, are precipitated from aloe vera juice and are mixed with a preservative, an antioxidant, a sweetener, and a flavorant to produce a palatable aloe vera beverage, carbonated or noncarbonated.

38 Claims, No Drawings

DRINK CONTAINING MUCILAGINOUS POLYSACCHARIDES AND ITS PREPARATION

REFERENCE TO RELATED APPLICATIONS

The present application is a continuation-in-part of U.S. application Ser. No. 07/864,583, filed Apr. 7, 1992 and entitled "Uses of Aloe Products," now U.S. Pat. No. 5,308,838 issued 3 May 1994 the entire contents and disclosure of which are hereby specifically incorporated by reference. Said U.S. application Ser. No. 07/864,583 is a divisional application of U.S. application Ser. No. 07/558,905, filed Jul. 27, 1990, and entitled "Uses of Aloe Products," granted on Jun. 2, 1992, as U.S. Pat. No. 5,118,673, the entire contents and disclosure of which are hereby specifically incorporated by reference, corresponds to International Application PCT/US91/08204, filed Nov. 5, 1991, and published under International. Publication No. WO 93/08810 on May 13, 1993, the entire contents and disclosure of which are also hereby specifically incorporated by reference. The said U.S. application Ser. No. 07/558,905 is a continuation-in-part of U.S. application Ser. No. 07/229,164, filed Aug. 5, 1988, and entitled "Administration of Acemannan," granted on Apr. 21, 1992, as U.S. Pat. No. 5,106,616. Said U.S. Pat. No. 5,106,616, the entire contents and disclosure of which are hereby specifically incorporated by reference, corresponds to International Application PCT/US89/03381, filed Aug. 3, 1989, and published under International Publication No. WO 90/01253 on Feb. 22, 1990, the entire contents and disclosure of which are also hereby specifically incorporated by reference. The said U.S. application Ser. No. 07/229,164 is a continuation-in-part of U.S. application Ser. No. 07/144,872, filed Jan. 14, 1988, and entitled "Process for Preparation of Aloe Products," granted on Jul. 25, 1989, as U.S. Pat. No. 4,851,224, the entire contents and disclosure of which are hereby specifically incorporated by reference. Said U.S. Pat. No. 4,851,224 is a continuation-in-part of U.S. application Ser. No. 06/869,261, filed on Jun. 5, 1986, and entitled "Processes for Preparation of Aloe Products, Products Produced Thereby and Compositions Thereof," granted on Apr. 5, 1988, as U.S. Pat. No. 4,735,935, the entire contents and disclosure of which are also hereby specifically incorporated by reference. Said U.S. Pat. No. 4,735,935, corresponds to International Application No. PCT/US86/01335, filed Jun. 20, 1986, and published under International Publication No. WO 87/00052 on Jan. 15, 1987, the entire contents and disclosure of which are also hereby specifically incorporated by reference. Said U.S. Pat. No. 4,735,935 is a continuation-in-part of U.S. application Ser. No. 06/810,025, filed Dec. 17, 1985 (now abandoned), which is a continuation-in-part of U.S. application Ser. No. 06/754,859, filed Jul. 12, 1985 (now abandoned) which is a continuation-in-part of U.S. application Ser. No. 06/750,321 filed Jun. 28, 1985 (now abandoned), which is a continuation-in-part of U.S. application Ser. No. 06/649,967 filed Sep. 12, 1984 (now abandoned), which is a continuation of U.S. application Ser. No. 06/375,720 filed May 7, 1982 (now abandoned). Application Ser. No. 06/810,025 is entitled "Processes for Preparation of Aloe Products and Products Produced Thereby." Applications Ser. Nos. 06/754,859; 06/750,321; 06/649,967; and 06/375,720 are entitled "Process for Preparation of Aloe Vera Products."

BACKGROUND

The present invention relates to a drink, or a concentrate that can be constituted with water to make a drink, containing aloe vera mucilaginous polysaccharides and its method of preparation from alcohol-precipitated mucilaginous polysaccharides derived from aloe vera leaves.

Aloe is a tropical or subtropical plant characterized by lance-shaped leaves with jagged edges and sharp points. For centuries, this plant has been considered to have, and has been used for its, medicinal and therapeutic properties without any clear understanding or scientific analysis of the bases for such properties.

Because of this lack of knowledge about the aloe plant and its characteristics, most methods employed for the processing of the plant and its components result in end products which do not consistently achieve desired results. Further, aloe leaves contain anthraquinones in its yellow sap. The anthraquinone-containing yellow sap is known to have a laxative effect with a reputation as an extremely irritating cathartic. Traditional processes for the production of various aloe products typically involved crushing (pressure rollers), grinding (e.g., use of Thompson aloe leaf slitter), or pressing (TCX pressure extruder) of the entire leaf of the aloe plant to produce an aloe vera juice, followed by various steps of filtration and stabilization of the juice. The resulting solution is then incorporated in, or mixed with, other solutions or agents to produce the products which could be, for example, a cosmetic, a health food drink, or a topical ointment. Unfortunately, because of improper processing procedures, many of these so-called aloe products contain no active ingredients, namely, mucilaginous polysaccharides (MP).

The principal disadvantage of such state of the art processes is the failure to recognize, and to take into account, that different components of the aloe leaf have characteristics that may not only be inconsistent with the intended use of the final product, but in many instances were deleterious to such use. Further, unless carefully controlled processes are used in processing the leaves of the aloe plant, the active ingredients, namely, mucilaginous polysaccharides, of the leaves are destroyed during the process.

These active polysaccharides have been identified, isolated and stabilized as described in U.S. Pat. Nos. 4,957,907 and 4,959,214, incorporated herein by reference. These active polysaccharides are hereinafter referred to as acemannan. Acemannan is an ordered linear polymer of substantially acetylated mannose monomers.

The physiological activity of acemannan and its pharmaceutical applications have been the object of numerous research studies at a number of laboratories, including Carrington Laboratories. These studies have primarily focused on the action of the activity of acemannan as an antiviral agent, an immunomodulator, a means of reducing opportunistic infections, and as a means of stimulating the healing processes.

Acemannan has been shown in laboratory studies to increase up to 300% in 48 hours the replication of fibroblasts in tissue culture which are known to be responsible for healing burns, ulcers and other wounds of the skin and of the gastrointestinal lining.

Acemannan has also been shown to increase DNA synthesis in the nucleus of fibroblasts. The increase in DNA synthesis in turn increases the rate of metabolic activity and cell replication which are fundamental steps in the healing process.

Acemannan has been shown in controlled studies to increase the rate of healing in animals.

Acemannan has also been shown to be an effective treatment for gastric ulcers in animal studies. Over a three year period, laboratory rats, the stomachs of which react similarly to that of humans, were tested. Acemannan was found to be equivalent to or superior to current medications used for the treatment of gastric ulcers. Most such products act to inhibit hydrochloric acid in the stomach. Acemannan works on a different principle and does not alter the natural flow of digestive acids.

Through the years, people have prepared health drinks containing aloe vera extracts. However, these drinks were never very popular because they have a bitter aftertaste and a laxative effect. Further, the majority of these drinks contain absolutely no active mucilaginous polysaccharides or acemannan.

U.S. Pat. No. 4,917,890, incorporated herein by reference, describes the preparation of an aloe vera drink utilizing a substantially anthraquinone-free aloe juice. This patent describes aloe juice that is prepared from aloe leaves by washing the leaves with a bactericidal solution, removing an anthraquinone-rich sap from the leaves by cutting off the tip of the leaf and draining the sap, removing the leaf rind to produce a substantially anthraquinone-free aloe gel fillet, and grinding the resulting aloe gel fillet to produce a substantially anthraquinone-free aloe juice. The described substantially anthraquinone-free aloe juice made up over 95% of the disclosed aloe drink.

The "aloe drink" of the present invention is a significant improvement over the currently commercially available aloe drinks, including the aloe drink described in the U.S. Pat. No. 4,917,890. The aloe drink of the U.S. Pat. No. 4,917,890 has a bitter aftertaste even after the drink has been supplemented with various flavoring agents. In fact, even when chilled, such drink still has an unpleasant aftertaste that many people cannot tolerate.

Furthermore, the aloe drink described in the U.S. Pat. No. 4,917,890 does not contain a consistent concentration of acemannan, the active ingredient of aloe juice. Seasonal rainfall variations are reflected in the acemannan content of aloe leaves. Therefore, depending on the rainfall at harvest, the concentration of acemannan in the extracted aloe juice used to make up the aloe drink described could vary significantly. Typically, the content of acemannan in the aloe drink prepared as described in U.S. Pat. No. 4,917,890 varies from about 500 mg to about 1500 mg per liter of the drink. Even at the lowest concentration of acemannan, i.e., at 500 mg of acemannan per liter of the drink, the bitter aftertaste is still present in such a drink.

Based on the foregoing, a need has arisen for a drink containing mucilaginous polysaccharides or acemannan that can be prepared having a known quantity of acemannan. The acemannan-containing drink should be easily produced by mixing water with an acemannan that is relatively stable at ambient temperatures. Furthermore, the drink should not leave a bitter aftertaste.

SUMMARY

The problems discussed above have been solved in the present invention which provides for an acemannan-containing drink, carbonated or noncarbonated, having a standardized quantity of acemannan and having essentially no aftertaste.

Broadly, one embodiment of the present invention is an aloe vera beverage comprising from about 0.01% to 0.5% weight percent of alcohol-precipitated mucilaginous polysaccharides derived from aloe vera leaves, with or without pulp.

A preferred embodiment of the present invention is an aloe vera beverage comprising aloe vera-derived mucilaginous polysaccharides, a sweetener, a preservative, an antioxidant, and a flavorant.

Accordingly, an object of the present invention is to provide a carbonated or noncarbonated drink that has mucilaginous polysaccharides derived from aloe vera leaves and that is relatively stable at room temperature.

Another object of the present invention is to provide a drink having a known quantity of acemannan.

Yet another object of the present invention is to provide an acemannan-containing drink with essentially no bitter aftertaste.

Still yet another object of the present invention is to provide an acemannan-containing drink that is palatable without added flavorings.

An additional object of the present invention is to provide an acemannan-containing drink that does not have to be cooled to be palatable.

Another object of the present invention is to provide a concentrate, or a relatively dry powder, that can be constituted with water to make a drink that contains aloe vera mucilaginous polysaccharides.

Other objects, advantages and novel features of the present invention will become apparent from the following description of the invention.

DETAILED DESCRIPTION

The problems discussed above, inherent in the previously available aloe drink have been solved in the embodiments of the present invention as described below.

One aspect of the present invention comprises a process for making a drink from mucilaginous polysaccharides derived from aloe leaves in the presence and absence of aloe pulp. The mucilaginous polysaccharides can be stored at room temperature and mixed with water to form a palatable drink.

Acemannan may be prepared as follows:

1. Aloe leaves are washed, sliced open and filleted to remove the leaf rind. The clean inner gel was retained while the green rind was discarded.

2. The filleted material was homogenized and extensively filtered with a Finisher Model 75 (FMC, Chicago, Ill.), to remove most of the pulp.

3. The clear viscous gel was acidified to a pH of approximately 3.2 with dilute HCl.

4. The acidified gel was then extracted for 4 to 5 hours with four volumes of 95% ethanol at ambient temperature. Floating fibers were removed, then the alcohol/water mixture was siphoned off while the solid precipitate was collected by centrifugation. Most alcohol/water soluble substances such as organic acids, oligosaccharides, monosaccharides, anthraquinones and inorganic salts are eliminated by the alcohol extraction process.

5. The solid aloe vera extract was then washed with fresh alcohol, centrifuged, freeze dried, and ground to a white powder. The acemannan at this stage still contains some protein, monosaccharides, oligosaccharides and inorganic salts. These contaminants do not affect the bioactivity of the acemannan and the acemannan can be stored as a source of bulk acemannan. The acemannan is stable at room temperature in the freeze-dried form for several years.

The detailed procedure for isolating the alcohol precipitate of aloe vera extract has been described in U.S. Pat. Nos. 4,957,907 and 4,959,214, the entire content of which is incorporated by reference.

A preferred embodiment of the present invention utilizes mucilaginous polysaccharides derived from aloe vera leaves by a process which varies from the procedure described above in that the viscous gel of step 3 was not acidified so that some of the organic acids remain in the gel. By not acidifying the gel a higher yield of mucilaginous polysaccharides is obtained. At this point, the aloe pulp or other fibers may also be added back in. Although optional, the aloe pulp may be added back into the aloe preparation to increase the fiber content and to improve the consistency of the aloe drink.

The viscous gel, with or without added pulp, was then extracted with four volumes of 95% ethanol, as described in step 4 above. The solid precipitate was collected by centrifugation. After centrifugation, the supernatant is decanted and discarded. Optionally, the precipitate may be washed with fresh alcohol and recentrifuged. The pellet is then freeze dried and ground into a powder. This preparation of alcohol-precipitated mucilaginous polysaccharides is hereinafter called Mucipol TM whether or not aloe vera pulp is present. The alcohol precipitation of the aloe vera mucilaginous polysaccharides (without added pulp) has been described in U.S. Pat. No. 4,735,935 incorporated herein by reference.

Mucipol TM extract is a freeze-dried aloe vera extract containing aloe vera mucilaginous polysaccharides, including acemannan, with or without aloe vera pulp. Acemannan is relatively pulp free. Mucipol TM extract can be assayed and standardized to contain specific amounts of acemannan and other polysaccharides of interest. When Mucipol TM extract is mixed with water to form an aloe drink, it produces a superior drink to that produced by aloe extracts currently available in the market or described in the patent literature.

Broadly, one embodiment of the present invention includes a mixture of Mucipol TM extract and water. The Mucipol TM extract is present in the present invention in amounts from about 0.001 to about 0.5 percent by weight, based on the total weight of the drink, and preferably from about 0.005 to about 0.2 percent by weight. An optimum concentration of Mucipol TM extract present in the aloe vera drink is about 0.1 percent by weight, based on the total weight of the drink. Similar concentrations of aloe vera mucilaginous polysaccharides, precipitated in the absence of aloe pulp, can also be used to make a palatable aloe drink. The drink can be carbonated if desired.

Preservatives, if desired, can be added into the aloe beverage of the present invention. Preservatives such as potassium sorbate, sodium benzoate, methylparaben and quaternary amines, such as benzalkonium chloride, may be used. Preferred preservatives such as potassium sorbate and sodium benzoate can be added from about 0.01 to about 1.0 weight percent based on the total weight of aloe drink.

A buffering agent such as citric or phosphoric acids and their salts can be used to maintain the pH of the beverage to a pH range of 2.5 to 6.0 and preferably at a pH of about 4.5.

A flavoring additive may be added to the aloe drink of the present invention. Such flavoring additives include spicy flavors, such as cinnamon or anise; fruity flavors, such as citrus fruits or extracts; botanical flavors, such as rose hip or vanilla; and synthetic flavorants. Flavorants may be derived from the natural edible fruits, spices and plants or from synthetically prepared flavors made to simulate natural flavorants. The amount of the flavorant used depends upon the flavor or flavors selected, the flavor impression desired, and the form of the flavor additive used. Commonly when a concentrated flavorant is used, the amount of flavorant added may vary from about 0.001 to about 10 percent by weight, based on the total weight of the drink. Alternatively, a fruit-flavored drink, a health drink, a sport drink and/or a natural vegetable or fruit juice, either dilute or concentrated, can be added to the drink of the present invention. The amount will depend on the desired flavor and taste.

The present invention may also contain a sweetener. Exemplary sweeteners include the carbohydrates fructose, maltose, sucrose, and dextrose. Carbohydrates, monosaccharides and oligosaccharides, are added from about a 0.5 to about a 14 percent by weight, based on the total weight of the drink, depending on the solubility of the sweetener. The amino acid glycine is a preferred sweetener and can be added to the beverage at about a 0.005 to about a 0.2 weight percent, based on the total weight of the drink. Glycine is preferably added at a 0.1 weight percent concentration.

For diet beverages, non-caloric or low-caloric sweeteners can be used. The low-caloric sweeteners can be derived either from natural origins or from synthetic sources. Examples of such non-caloric or low-caloric sweeteners include, but are not limited to, saccharin, cyclamates, acetosulfam, sorbitol, xylitol, L-aspartyl-L-phenyl-alanine ester (e.g. aspartame), etc. The amount of the non-caloric sweetener used depends on the particular sweetener, or mixture of sweeteners, and the sweetness intensity desired. Generally, the non-caloric or low-caloric sweetener ranges from about 0.5 to about 14 weight percent, based on the total weight of the drink.

An antioxidant can also be added to the aloe vera drink. Exemplary antioxidants are sodium metabisulfite, Vitamin E, citric acid, or mixtures thereof. Sodium metabisulfite is the preferred antioxidant and may be included in the composition at from about 0.01 to about 0.1 percent by weight based on the total weight of the drink.

Vitamins, such as Vitamin C, E, or $B_{12}$, and minerals may also be added to the aloe vera beverage as desired. Among the major physiological electrolytes that can be used in this application are sodium, potassium, chloride calcium, magnesium, iron and others.

The electrolytes and ionic components usable for the present invention are usually obtainable from their corresponding water-soluble and non-toxic salts. Unless otherwise defined, the amount of electrolytes or ionic components in the beverage is based on those present in the final drinkable beverage composition. Some of the less soluble salts must be "solubilized" in water, or in water having an acidic pH, in order to be useful in the present invention. For example, "solubilized calcium" means calcium ions dissolved. The ionic components indicate the components obtained when dissolved in water or acidified water.

The sodium ion component can be obtained from any readily available sodium salt, such as the chloride, carbonate, bicarbonate, citrate, phosphate, hydrogen phosphate, tartrate, benzoate and the like, or a combination thereof.

Likewise, the potassium ion component can be provided by any salt such as the chloride, bicarbonate, citrate, phosphate, hydrogen phosphate, tartrate, sorbate and the like, or a combination thereof.

The chloride ion component can be provided by a salt such as sodium chloride or potassium chloride.

The bicarbonate ion component that can be used in the present invention can be obtained from their corresponding sodium or potassium salts, among others.

The phosphate ions usable for the present invention can be obtained from dissolution of hydrated disodium hydrogen phosphate and hydrated sodium dihydrogen phosphate in an aqueous solution.

The solubilized iron usable for the present invention can be obtained from any suitable ferrous salts, such as ferrous sulfate, ferrous fumarate, ferrous gluconate, or mixture thereof. The amount of solubilized iron selected is an amount that is below a subjective taste threshold.

The solubilized magnesium usable for the present invention can be obtained from a salt such as magnesium citrate, magnesium oxide, magnesium aspartate, magnesium chloride, or magnesium sulfate.

The solubilized calcium that may be used in the present invention can be supplied by calcium carbonate, calcium phosphate, calcium hydrogen phosphate, calcium dihydrogen phosphate, calcium hydroxide, calcium chloride dehydrate, calcium sulfate, as well as the respective sour salts of calcium, such as, calcium citrate, calcium malate, calcium ascorbate, or calcium orotate, and mixture thereof.

If desired, coloring agents can also be added into the aloe beverage of the present invention. Any soluble coloring agents approved for food use can be utilized for the present invention.

The aloe vera beverage of the present invention was prepared by mixing the Mucipol TM extract with water by stirring with a mechanical homogenizer. As the aloe extract was agitated, the other ingredients were added and the mixture was continually agitated until all of the ingredients had gone into solution. The beverage may be carbonated or noncarbonated.

EXAMPLE 1

A drinkable aloe vera beverage was prepared as follows:

| Ingredient | Amount Added |
| --- | --- |
| Mucipol TM extract | 1000 mg |
| Deionized water | 1000 ml |

The mixture was blended with a mechanical homogenizer until the Mucipol TM extract was dissolved.

A drinkable aloe vera beverage may also be prepared by mixing alcohol-precipitated aloe vera mucilaginous polysaccharides prepared without pulp with water at the same concentration as Mucipol TM extract.

EXAMPLE 2

A drinkable aloe vera beverage was prepared containing the following ingredients:

| Ingredient | Amount Added | % Weight Based On Total Drink |
| --- | --- | --- |
| Mucipol TM extract | 379.0 grams | 0.1% |
| deionized water | 152.0 liters | 99.31% |
| sodium benzoate | 379.0 grams | 0.1% |
| glycine | 3.0 kg | 0.1% |
| citric acid FCC, USP | 417.0 grams | 0.1% |
| potassium sorbate USP | 190.0 grams | 0.1% |
| Vitamin E FCC | 1 gm/100 gal. | |
| sodium metabisulfite | 76.0 grams | 0.02% |
| vanilla | 121.0 grams | 0.032% |
| cinnamon oil | 8.0 mls | 0.002% |
| lime juice | 200.0 mls | 0.053% |
| Adams Best Lemon Extract | 308.0 mls | 0.081% |

The Mucipol TM extract was initially homogenized with water. As the mixture continued to be mixed, the other ingredients were added and the mixture was continually mixed until all ingredients had gone into solution.

An aloe vera beverage may also be prepared as described in Example 2, substituting alcohol-precipitated mucilaginous polysaccharides (without added pulp) in place of the Mucipol TM extract. The mucilaginous polysaccharide precipitate is added to the composition at the same concentration as Mucipol TM extract.

EXAMPLE 3

Another drinkable aloe vera beverage was prepared containing the following ingredients:

| Ingredient | % Weight Based On Total Drink |
| --- | --- |
| Mucipol TM extract | 0.1% |
| deionized water | 99.328% |
| sodium benzoate | 0.1% |
| glycine | 0.1% |
| citric acid FCC, USP | 0.1% |
| potassium sorbate USP | 0.1% |
| Vitamin E FCC | |
| sodium metabisulfite | 0.02% |
| vanilla | 0.017% |
| cinnamon oil | 0.001% |
| lime juice | 0.053% |
| Adams Best Lemon Extract | 0.081% |

The Mucipol TM extract was initially homogenized with water. As the mixture continued to be mixed, the other ingredients were added and the mixture was continually mixed until all ingredients had gone into solution.

An aloe vera beverage may also be prepared as described in Example 3, substituting alcohol-precipitated mucilaginous polysaccharides (without added pulp) in place of the Mucipol TM extract. The mucilaginous polysaccharide precipitate is added to the composition at the same concentration as Mucipol TM extract.

One way to prepare the concentrate form of the liquid beverage would be to start with less than the required volume of the liquid solvent that is used in the preparation of the drinkable beverage. Another way would be to partially dehydrate the finally prepared drinkable beverage to remove only a portion of the liquid solvent and any other volatile liquids present. Dehydration can be accomplished in accordance with a well-known procedure, such as evaporation under vacuum. The concentrate can be in the form of a relatively thick, syrupy liquid or a solid. The solid can be in the form of an essentially dry powder or a tablet. The concentrate can later be constituted with a proper amount of water to make the final drinkable beverage.

Carbon dioxide can be introduced either into the water to be mixed with the beverage concentrate, or into the drinkable beverage, to achieve carbonation. The carbonated beverage can then be stored in a container, such as a bottle or a can and then sealed. See L. F. Green, Development in Soft Drinks Technology, Vol. 1, pp. 102–107, Applied Science Publishers Ltd., 1978, herein incorporated by reference. The amount of carbon dioxide introduced into the beverage composition depends upon the particular flavor system used and the amount of carbonation desired. Usually, carbonated beverages of the present invention contain from about 1.0 to about 4.5 volumes of carbon dioxide. Preferred carbonated beverages contain from about 2 to about 3.5 volumes of carbon dioxide.

The essentially dry mixture of the beverage can be prepared by blending the proper amounts and ratios of all the required dry ingredients together. Alternatively, the finally prepared drinkable beverage composition can be dehydrated to give the essentially dry mixture of the beverage composition. Multodextrin, or an edible binding agent, such as starch, can be added to a powder form of the beverage composition and the resulting mixture compacted into tablets. The essentially dry mixture, either as powder, granules or tablets, can later be dissolved in a proper amount of water, carbonated or noncarbonated, to make the final drinkable beverage.

The essential ingredient in the concentrate or essentially dry powder or tablet is aloe vera mucilaginous polysaccharides, with or without pulp, or acemannan. One or more of the ingredients described above may be added to the mucilaginous polysaccharides or acemannan to make the concentrate or essentially dry powder or tablet. A preservative, however, is generally not required in the concentrate or, in particular, in the essentially dry powder or tablet.

In a taste test, five individuals were asked to compare the taste of a drink made with the previously described substantially anthraquinone-free aloe juice to a drink made with alcohol-precipitated mucilaginous polysaccharides, or Mucipol ™, as described in Example 1. The drink made with Mucipol ™ contained about 1000 mg of acemannan per liter of the drink and contained no flavoring additives. The drink made with substantially anthraquinone-free aloe juice has been described in U.S. Pat. No. 4,917,890. This aloe drink made with substantially anthraquinone-free aloe juice contained various flavorings and the concentration of acemannan was about 1000 mg per liter of the drink. The tests involved drinks prepared from two different aloe materials and were served at room temperature and served chilled. Each of the five people found the Mucipol ™ drink to be much more palatable. The drink made with a substantially anthraquinone-free aloe juice was found to have a bitter aftertaste. Even when chilled, the drink made from the substantially anthraquinone-free aloe juice was found to still have a bitter aftertaste. The chilling did mask the bitter aftertaste a little, but not enough to make it very palatable. In contrast, the drink made from Mucipol ™, although it contained no flavoring additive at all, did not have to be chilled and had no aftertaste. It was palatable even at room temperature.

While preferred embodiments of the aloe vera drink have been disclosed, it will be apparent to those skilled in the art that numerous modifications and variations are possible in light of the above teaching. It should also be realized by those skilled in the art that such modifications and variations do not depart from the spirit and scope of the invention as set forth in the appended claims.

We claim:

1. A drank comprising:
   from about 0.001 to about 0.5 weight percent, based on total weight of the drink, of aloe vera mucilaginous polysaccharides prepared by the process of: removing leaf rind of an aloe vera leaf to give an aloe vera gel; grinding said aloe vera gel to give an aloe vera juice; adding a water-soluble lower aliphatic polar solvent to said aloe vera juice to give said aloe vera mucilaginous polysaccharides; and isolating and drying said aloe vera mucilaginous polysaccharides; and
   water.

2. The drink as recited in claim 1, wherein said mucilaginous polysaccharides comprise from about 0.005 to about 0.2 weight percent of the drink.

3. The drink as recited in claim 1, wherein said mucilaginous polysaccharides comprise about 0.1 weight percent of the drink.

4. The drink as recited in claim 1, further comprising of pulp of aloe vera.

5. The drink as recited in claim 1, further comprising from about 0.001 to about 1 weight percent of a preservative.

6. The drink as recited in claim 5, wherein said preservative is selected from the group consisting of potassium sorbate, sodium benzoate, quaternary amine, and methylparaben.

7. The drink as recited in claim 1, further comprising a buffering agent to maintain a pH from about 2.5 to about 6.0.

8. The drink as recited in claim 1, further comprising a buffering agent to maintain a pH of about 4.5.

9. The drink as recited in claim 1, further comprising a flavoring additive.

10. The drink as recited in claim 9, wherein said flavoring additive is selected from the group consisting of cinnamon oil, vanilla, citric acid, fruit juice, and fruit extract.

11. The drink as recited in claim 1, further comprising a sweetener.

12. The drink as recited in claim 11, wherein said sweetener is selected from the group consisting of fructose, sucrose, dextrose, and glycine.

13. The drink as recited in claim 11, wherein said sweetener is a low caloric sweetener.

14. The drink as recited in claim 13, wherein said low caloric sweetener is selected from the group consisting of saccharin, cyclamate, and aspartame.

15. The drink as recited in claim 1, further comprising a natural juice.

16. The drink as recited in claim 1, wherein said drink is carbonated.

17. The drink as recited in claim 1, further comprising an antioxidant.

18. The drink as recited in claim 17, wherein said antioxidant is sodium metabisulfite.

19. The drink as recited in claim 17, wherein said antioxidant is d-alpha tocopheryl acetate.

20. The drink as recited in claim 1, further comprising a vitamin.

21. The drink as recited in claim 1, further comprising an electrolyte.

22. A drink comprising:
aloe vera mucilaginous polysaccharides prepared by the process of: removing leaf rind of an aloe vera leaf to give an aloe vera gel; grinding said aloe vera gel to give an aloe vera juice; adding a water-soluble lower aliphatic polar solvent to said aloe vera juice to give said aloe vera mucilaginous polysaccharides; and isolating and drying said aloe vera mucilaginous polysaccharides;
a preservative;
an antioxidant;
a sweetener; and
a flavorant.

23. A drink comprising:
acemannan;
a preservative;
an antioxidant;
a sweetener; and
a flavorant.

24. The drink as recited in claim 23, further comprising pulp of aloe vera.

25. A drink comprising:
about 0.1 weight percent, based on total weight of the drink, of an aloe vera mucilaginous polysaccharides prepared by the process of: removing leaf rind of an aloe vera leaf to give an aloe vera gel; grinding said aloe vera gel to give an aloe vera juice; adding a water-soluble lower aliphatic polar solvent to said aloe vera juice to give said aloe vera mucilaginous polysaccharides; and isolating and drying said aloe vera mucilaginous polysaccharides;
about 0.1 weight percent, based on total weight of the drink, of sodium benzoate;
about 0.1 weight percent, based on total weight of the drink, of glycine;
about 0.1 weight percent, based on total weight of the drink, of citric acid;
about 0.1 weight percent, based on total weight of the drink, of potassium sorbate;
about 0.02 weight percent, based on total weight of the drink, of sodium metabisulfite;
about 10 milligrams of Vitamin E per gallon of the drink;
about 0.032 weight percent, based on total weight of the drink, of vanilla;
about 0.002 weight percent, based on total weight of the drink, of cinnamon oil;
about 0.053 weight percent, based on total weight of the drink, of lime juice;
about 0.081 weight percent, based on total weight of the drink, of lemon extract; and
water.

26. The drink as recited in claim 25, further comprising pulp of aloe vera.

27. A drink comprising:
about 0.1 weight percent, based on total weight of the drink, of an aloe vera mucilaginous polysaccharides prepared by the process of: removing leaf rind of an aloe vera leaf to give an aloe vera gel; grinding said aloe vera gel to give an aloe vera juice; adding a water-soluble lower aliphatic polar solvent to said aloe vera juice to give said aloe vera mucilaginous polysaccharides; and isolating and drying said aloe vera mucilaginous polysaccharides;
about 0.1 weight percent, based on total weight of the drink, of sodium benzoate;
about 0.1 weight percent, based on total weight of the drink, of glycine;
about 0.1 weight percent, based on total weight of the drink, of citric acid;
about 0.1 weight percent, based on total weight of the drink, of potassium sorbate;
about 0.02 weight percent, based on total weight of the drink, of sodium metabisulfite;
about 10 milligrams of Vitamin E per gallon of the drink;
about 0.017 weight percent, based on total weight of the drink, of vanilla;
about 0.001 weight percent, based on total weight of the drink, of cinnamon oil;
about 0.053 weight percent, based on total weight of the drink, of lime juice;
about 0.081 weight percent, based on total weight of the drink, of lemon extract; and
water.

28. The drink as recited in claim 27, further comprising pulp of aloe vera.

29. A process for making an aloe vera beverage containing a quantity of acemannan, said process comprising the steps of:
washing an aloe leaf in a bactericidal solution to remove substantially all surface dirt and bacteria;
filleting said aloe leaf to produce an aloe gel fillet;
grinding and homogenizing said aloe gel fillet to give a homogenate;
extracting said homogenate with a lower aliphatic alcohol;
removing the pulpy acemannan-containing precipitate;
lyophilizing the pulpy acemannan-containing precipitate; and
dispersing said lyophilized precipitate in water at an ambient temperature.

30. The process for making an aloe vera beverage of claim 27, further comprising the step of concentrating said homogenate by ultrafiltration before extracting said homogenate with a lower aliphatic alcohol.

31. The drink as recited in claim 1, wherein said water-soluble lower aliphatic polar solvent comprises a lower aliphatic alcohol.

32. The drink as recited in claim 22, wherein said water-soluble lower aliphatic polar solvent comprises a lower aliphatic alcohol.

33. The drink as recited in claim 25, wherein said water-soluble lower aliphatic polar solvent comprises a lower aliphatic alcohol.

34. The drink as recited in claim 27, wherein said water-soluble lower aliphatic polar solvent comprises a lower aliphatic alcohol.

35. The drink as recited in claim 1, wherein said drying comprises lyophilizing.

36. The drink as recited in claim 22, wherein said drying comprises lyophilizing.

37. The drink as recited in claim 25, wherein said drying comprises lyophilizing.

38. The drink as recited in claim 27, wherein said drying comprises lyophilizing.

* * * * *

UNITED STATES PATENT AND TRADEMARK OFFICE
CERTIFICATE OF CORRECTION

PATENT NO. : 5,443,830
DATED : August 22, 1995
INVENTOR(S) : Moore et al.

It is certified that error appears in the above-indentified patent and that said Letters Patent is hereby corrected as shown below:

Col. 1, line 20, following "International", delete ".".

Col. 10, line 13, delete "drank" and insert therefore -- drink --.

Col. 10, line 32, delete "of".

Signed and Sealed this

Twelfth Day of March, 1996

Attest:

BRUCE LEHMAN

*Attesting Officer*  *Commissioner of Patents and Trademarks*